US011013452B1

(12) United States Patent
Song et al.

(10) Patent No.: US 11,013,452 B1
(45) Date of Patent: May 25, 2021

(54) ARTIFICIAL INTELLIGENCE (AI) BASED PARKINSON'S DISEASE DIAGNOSING APPARATUS AND METHOD

(71) Applicant: Heuron Co., Ltd., Incheon (KR)

(72) Inventors: Soo Hwa Song, Uijeongbu-si (KR); Hwan Heo, Seongnam-si (KR)

(73) Assignee: Heuron Co., Ltd., Incheon (KR)

(*) Notice: Subject to any disclaimer, the term of this patent is extended or adjusted under 35 U.S.C. 154(b) by 0 days.

(21) Appl. No.: 16/893,702

(22) Filed: Jun. 5, 2020

(30) Foreign Application Priority Data

Mar. 3, 2020 (KR) .................. 10-2020-0026561

(51) Int. Cl.
*A61B 5/055* (2006.01)
*G06T 7/00* (2017.01)
(Continued)

(52) U.S. Cl.
CPC .......... *A61B 5/4082* (2013.01); *A61B 5/0042* (2013.01); *A61B 5/055* (2013.01);
(Continued)

(58) Field of Classification Search
CPC ..... A61B 5/4082; A61B 5/7267; A61B 5/055; A61B 5/0042; A61B 5/7282;
(Continued)

(56) References Cited

U.S. PATENT DOCUMENTS

| 2012/0321162 | A1* | 12/2012 | Liu | .................... | G01R 33/5616 |
| | | | | | 382/131 |
| 2013/0322723 | A1* | 12/2013 | Akhbardeh | ............. | G06T 7/337 |
| | | | | | 382/131 |

(Continued)

FOREIGN PATENT DOCUMENTS

| CN | 106898000 A | * 6/2017 | ............... G06T 7/10 |
| CN | 109242849 A | 1/2019 | |

(Continued)

OTHER PUBLICATIONS

Schwarz et al. "The 'Swallow Tail' Appearance of the Healthy Nigrosome—A New Accurate Test of Parkinson's Disease: A Case-Control and Retrospective Cross-Sectional MRI Study at 3T." PLoS One. 2014; 9(4): e93814. Published online Apr. 7, 2014.*

(Continued)

*Primary Examiner* — Amanda Lauritzen Moher
(74) *Attorney, Agent, or Firm* — Sughrue Mion, PLLC

(57) ABSTRACT

The present invention relates to an artificial intelligence-based Parkinson's disease diagnosing apparatus and method. An artificial intelligence-based Parkinson's disease diagnosing apparatus which is an aspect of the present disclosure includes an image acquiring unit which acquires a first image related to a multi-echo magnitude and phase from an MRI obtained by capturing a brain of a patient; an image processing unit which post-processes the acquired first image so as to observe a substantia nigra and a nigrosome-1 region used as imaging biomarkers of the Parkinson's disease; an image analyzing unit which analyzes the post-processed first image to classify a second image including the nigrosome-1 region and detects the nigrosome-1 region from the classified second image; and a diagnosing unit which diagnoses whether the patient has the Parkinson's disease by analyzing whether the detected nigrosome-1 region is normal, in which the image processing unit generates a susceptibility map weighted imaging image by applying a quantitative susceptibility map mask to the first image based on a quantitative susceptibility mapping algorithm to perform the post-processing and the image processing unit further performs at least one operation of angle adjustment, image enlargement, and reslice, on the generated susceptibility map weighted imaging image.

12 Claims, 13 Drawing Sheets

(51) Int. Cl.
   *A61B 5/00*    (2006.01)
   *G06K 9/62*    (2006.01)
   *G06K 9/32*    (2006.01)
   *G06T 3/40*    (2006.01)
   *G16H 50/20*   (2018.01)
   *G16H 30/40*   (2018.01)
   *G16H 30/20*   (2018.01)
   *G16H 10/40*   (2018.01)
   *G06N 3/04*    (2006.01)
   *G06N 3/08*    (2006.01)
   *G01R 33/20*   (2006.01)

(52) U.S. Cl.
   CPC .......... *A61B 5/7267* (2013.01); *A61B 5/7282* (2013.01); *G06K 9/3208* (2013.01); *G06K 9/6267* (2013.01); *G06N 3/04* (2013.01); *G06N 3/08* (2013.01); *G06T 3/40* (2013.01); *G06T 7/0012* (2013.01); *G16H 10/40* (2018.01); *G16H 30/20* (2018.01); *G16H 30/40* (2018.01); *G16H 50/20* (2018.01); *A61B 2576/026* (2013.01); *G01R 33/20* (2013.01); *G06K 2209/051* (2013.01); *G06T 2207/10088* (2013.01); *G06T 2207/20016* (2013.01); *G06T 2207/20081* (2013.01); *G06T 2207/20084* (2013.01); *G06T 2207/30016* (2013.01)

(58) Field of Classification Search
   CPC .. A61B 2576/026; G16H 30/20; G16H 50/20; G16H 10/40; G16H 30/40; G06N 3/04; G06N 3/08; G06T 7/0012; G06T 2207/20081; G06T 2207/10088; G06T 2207/30016; G06T 2207/20016; G06T 2207/20084; G06T 3/40; G06K 2209/051; G06K 9/6267; G06K 9/3208
   See application file for complete search history.

(56) References Cited

U.S. PATENT DOCUMENTS

| | | | | |
|---|---|---|---|---|
| 2015/0012466 A1* | 1/2015 | Sapiro | ................... | G06N 20/00 706/12 |
| 2016/0054410 A1* | 2/2016 | Schenck | .............. | A61B 5/4076 600/410 |
| 2017/0261584 A1 | 9/2017 | James et al. | | |
| 2019/0261906 A1* | 8/2019 | Shirai | ................ | A61B 5/14542 |
| 2020/0264253 A1* | 8/2020 | Shin | ....................... | G06T 11/008 |
| 2021/0007603 A1* | 1/2021 | Huddleston | ............ | G16H 50/20 |

FOREIGN PATENT DOCUMENTS

| | | | | |
|---|---|---|---|---|
| KR | 10-2016-0058812 A | | 5/2016 | |
| KR | 10-1754291 B1 | | 7/2017 | |
| WO | WO-2018083952 A1 * | | 5/2018 | ......... A61B 5/14551 |

OTHER PUBLICATIONS

Xu et al. "Use of Magnetic Resonance Imaging and Artificial Intelligence in Studies of Diagnosis of Parkinson's Disease." ACS Chem. Neurosci. 2019, 10, 2658-2667. Published May 14, 2019.*

Cheng et al. "Radiomic Features of the Nigrosome-1 Region of the Substantia Nigra: Using Quantitative Susceptibility Mapping to Assist the Diagnosis of Idiopathic Parkinson's Disease." Front. Aging Neurosci Published Jul. 16, 2019.*

Xiao et al. "Quantitative susceptibility mapping based hybrid feature extraction for diagnosis of Parkinson's disease." NeuroImage: Clinical. vol. 24, 2019. Published Nov. 5, 2019.*

Mohsen et al. "Location Sensitive Deep Convolutional Neural Networks for Segmentation of White Matter Hyperintensities." Scientific Reports | 7: 5110. Published online Jul. 11, 2017.*

Li et al. "FRD-CNN: Object detection based on small-scale convolutional neural networks and feature reuse." Scientific Reports | (2019) 9:16294. Published Nov. 8, 2019.*

EPO machine translation of CN 109242849, generated Mar. 11, 2021.*

Christian Langkammer et al., "Quantitative susceptibility mapping (QSM) as a means to measure brain iron? A post mortem validation study", Neuroimage, Sep. 2012, pp. 1593-1599, vol. 62, No. 3-2.

Sung-Min Gho et al., "Susceptibility Map-Weighted Imaging (SMWI) for Neuroimaging", Magnetic Resonance in Medicine, 2014, pp. 337-346, vol. 72.

Yoonho Nam, Phd et al., "Imaging of Nigrosome 1 in Substantia Nigra at 3T Using Multiecho Susceptibility Map-Weighted Imaging (SMWI)", Journal of Magnetic Resonance Imaging, Aug. 2017, pp. 528-536, vol. 46.

Korean Notice of Allowance for 10-2020-0026561 dated Mar. 26, 2020.

* cited by examiner (a)          (b)          (c)

ARTIFICIAL INTELLIGENCE (AI) BASED PARKINSON'S DISEASE DIAGNOSING APPARATUS AND METHOD

CROSS-REFERENCE TO RELATED APPLICATIONS

This application claims the priority of Korean Patent Application No. 10-2020-0026561 filed on Mar. 3, 2020 in the Korean Intellectual Property Office, the disclosure of which is incorporated herein by reference.

BACKGROUND

Field

The present disclosure relates to an artificial intelligence-based Parkinson's disease diagnosing apparatus and method, and more particularly, to a Parkinson's disease diagnosing apparatus and method which diagnose the Parkinson's disease by analyzing magnetic resonance imaging (hereinafter, abbreviated as "MRI").

Description of the Related Art

The neurodegenerative disorder refers to a disease which causes an abnormal brain function as nerve cells die due to some reasons.

Representative neurodegenerative disorders usually include Alzheimer's disease, Parkinson's disease, and rarely, Lou Gehrig's disease.

Among the neurodegenerative disorders, the Parkinson's disease is a representative neurodegenerative disorder by which neural cells are destroyed and is accompanied by depression and anxiety together with symptoms such as rigidity, hand and foot tremors, and difficulty in walking so that the quality of life is greatly degraded.

The neurodegenerative disorder is diagnosed by a non-invasive method of diagnosing without contact with mucosa, skin break, and internal body cavity beyond a natural or artificial body orifice.

For example, in the following Patent Documents 1 and 2, a technology of diagnosing the neurodegenerative disorder according to the related art is disclosed.

RELATED ART DOCUMENT

Patent Document

1. Korean Registered Patent No. 10-1754291 (published on Jul. 6, 2017)
2. Korean Unexamined Patent Application Publication No. 10-2016-0058812 (published on May 25, 2016)

Non-Patent Document

1. Sung-Min Gho et al., "Susceptibility Map-Weighted Imaging (SMWI) for Neuroimaging", Magnetic Resonance in Medicine 72:337-346(2014)
2. Yoonho Nam et al., "Imaging of Nigrosome 1 in Substantia Nigra at 3T Using Multiecho Susceptibility Map-Weighted Imaging (SMWI)", J. MAGN. RESON. IMAGING 2017; 46:528-536
3. Christian Langkammer et al., "Quantitative susceptibility mapping (QSM) as a means to measure brain iron? A post mortem validation study", Neuroimage. 2012 September; 62(3):1593-9. doi: 10.1016/j.neuroimage. 2012.05.049. Epub 2012 May 24.

SUMMARY

Until now, [18F]FP-CIT Positron emission tomography (PET) using isotopes has been used as the most objective method for a diagnosis of Parkinson's disease and a differential diagnosis of drug-induced Parkinsonism.

However, [18F]FP-CIT PET is a very expensive test method and has a risk of radiation exposure.

Therefore, it is requested to develop a technology of diagnosing the Parkinson's disease by observing a nigrosome-1 region using the MRI.

An object of the present invention is to solve the problems as described above and to provide a Parkinson's disease diagnosing apparatus and method which diagnose the Parkinson's disease by analyzing the MRI.

Another object of the present invention is to provide a Parkinson's disease diagnosing apparatus and method which diagnose the Parkinson's disease by analyzing a nigrosome-1 region proposed as imaging biomarkers for the Parkinson's disease.

Further, an object of the present disclosure is to provide a Parkinson's disease diagnosing apparatus and method which are capable of observing only a substantia nigra and a nigrosome-1 region proposed as imaging biomarkers for the Parkinson's disease from an acquired image by additionally performing a pre-processing process, such as angle adjustment, image enlargement, and reslice, on an SMWI image.

Further, an object of the present disclosure is to provide a Parkinson's disease diagnosing apparatus and method which effectively detect a nigrosome-1 region by detecting a red nucleus and substantia nigra which are more easily detected therearound through machine learning and detecting an image at a moment when both red nucleus and substantia nigra are present and then the red nucleus disappears.

Furthermore, an object of the present disclosure is to provide a Parkinson's disease diagnosing apparatus and method which decide a final diagnosis as to whether a patient is normal or has a Parkinson's disease according to the majority rule when a plurality of learning models is generated using the same data set and a predictive diagnosis result is derived by applying the plurality of learning models, respectively, and diagnosis results between the plurality of learning models are different.

Further, an object of the present disclosure is to provide a device, a system, and a method which increase a probability of successful clinical trials by utilizing a Parkinson's disease diagnosing method using artificial intelligence to screen a patient group and a normal group.

In the meantime, technical objects to be achieved in the present invention are not limited to the aforementioned technical objects, and another not-mentioned technical object will be obviously understood by those skilled in the art from the description below.

In order to achieve the above-described technical objects, an artificial intelligence-based Parkinson's disease diagnosing apparatus which is an aspect of the present disclosure includes an image acquiring unit which acquires a first image related to a multi-echo magnitude and phase from an MRI obtained by capturing a brain of a patient; an image processing unit which post-processes the acquired first image so as to observe a substantia nigra and a nigrosome-1 region used as imaging biomarkers of the Parkinson's disease; an image analyzing unit which analyzes the post-processed first image to classify a second image including the nigrosome-1 region and detects the nigrosome-1 region from the classified second image; and a diagnosing unit which diagnoses whether the patient has the Parkinson's disease by analyzing whether the detected nigrosome-1 region is normal, in which the image processing unit generates a susceptibility map weighted imaging image by applying a quantitative susceptibility map mask to the first image based on a quantitative susceptibility mapping algorithm to perform the post-processing and the image processing unit further performs at least one operation of angle adjustment, image enlargement, and reslice, on the generated susceptibility map weighted imaging image.

Further, the angle adjustment is an operation of correcting a misalignment of the generated susceptibility map weighted imaging image so as to easily observe the nigrosome-1 region, the image enlargement is an operation of enlarging an image related to the nigrosome-1 region, and the reslice may be an operation of increasing the number of generated first images including the nigrosome-1 region.

Further, the image analyzing unit may detect a red nucleus and a substantia nigra present in the post-processed first image through machine learning and classify a second image including the nigrosome-1 region based on an image at a moment when the red nucleus between the detected red nucleus and the substantia nigra disappears from the first image.

The image analyzing unit may analyze an image within a predetermined range from the image, in the first image to classify a second image including the nigrosome-1 region.

The image analyzing unit may classify the second image including the nigrosome-1 region using a one-stage detector method among methods using a deep learning neural network of machine learning.

The image analyzing unit may detect a feature map having a feature of a fully convolutional layer by applying a convolutional neural network (CNN) to the post-processed first image, derive cross-scale connections by applying a feature pyramid network (FPN) to the feature map, and adjust a classification loss, a bounding-box regression loss, and a focal loss for a classification result based on the cross-scale connections, in accordance with a predetermined criterion, to classify the second image including the nigrosome-1 region.

Further, the diagnosing unit may generate a plurality of learning models to diagnose whether it is the Parkinson's disease, based on the same data set, derive a plurality of predictive results by the plurality of learning models, based on the detected nigrosome-1 region, and diagnose whether the patient has the Parkinson's disease based on the plurality of predictive results.

The diagnosing unit may diagnose whether the patient has the Parkinson's disease based on predictive results which occupy the majority, by applying the majority rule to the plurality of predictive results by the plurality of learning models, based on the detected nigrosome-1 region.

In order to achieve the above-described technical objects, an artificial intelligence-based Parkinson's disease diagnosing method which is another aspect of the present disclosure includes a first step of acquiring a first image related to a multi-echo magnitude and phase from an MRI obtained by capturing a brain of a patient, by an image acquiring unit; a second step of post-processing the acquired first image so as to observe a substantia nigra and a nigrosome-1 region used as imaging biomarkers of the Parkinson's disease, by an image processing unit; a third step of analyzing the post-processed first image to classify a second image including the nigrosome-1 region, by an image analyzing unit; a fourth step of detecting the nigrosome-1 region from the classified second image, by an image analyzing unit; and a fifth step of diagnosing whether the patient has the Parkinson's disease by analyzing whether the detected nigrosome-1 region is normal, by a diagnosing unit in which in the second step, the image processing unit generates a susceptibility map weighted imaging image by applying a quantitative susceptibility map mask to the first image based on a quantitative susceptibility mapping algorithm to perform the post-processing and between the second step and the third step, the method may further include a 2.5-th step of further performing at least one operation of angle adjustment, image enlargement, and reslice, on the generated susceptibility map weighted imaging image, by the image processing unit.

In the 2.5-th step, the angle adjustment is an operation of correcting a misalignment of the generated susceptibility map weighted imaging image so as to easily observe the nigrosome-1 region, the image enlargement is an operation of enlarging an image related to the nigrosome-1 region, and the reslice is an operation of increasing the number of generated first images including the nigrosome-1 region.

The third step may further include a 3-1-th step of detecting a red nucleus and a substantia nigra present in the post-processed first image by machine learning, by the image analyzing unit; and a 3-2-th step of classifying a second image including the nigrosome-1 region based on an image at a moment when the red nucleus between the detected red nucleus and substantia nigra disappears from the first image, by the image analyzing unit.

Further, in the 3-2-th step, the image analyzing unit may analyze an image within a predetermined range from the first image, in the image to classify a second image including the nigrosome-1 region.

In the third step, the image analyzing unit may classify the second image including the nigrosome-1 region using a one-stage detector method among methods using a deep learning neural network of machine learning.

The third step may further include: a 3-1-th step of detecting a feature map having a feature of a fully convolutional layer by applying a convolutional neural network (CNN) to the post-processed first image, by the image analyzing unit; a 3-2-th step of deriving cross-scale connections by applying a feature pyramid network (FPN) to the feature map, by the image analyzing unit; and a 3-3-th step of adjusting a classification loss, a bounding-box regression loss, and a focal loss for a classification result based on the cross-scale connections, in accordance with a predetermined criterion, to classify the second image including the nigrosome-1 region, by the image analyzing unit.

Further, the fifth step includes a 5-1-th step of generating a plurality of learning models to diagnose whether it is the Parkinson's disease, based on the same data set, by the diagnosing unit, a 5-2-th step of deriving a plurality of predictive results by the plurality of learning models, based on the detected nigrosome-1 region, by the diagnosing unit; and a 5-3-th step of diagnosing whether the patient has the Parkinson's disease based on the plurality of predictive results, by the diagnosing unit.

Further, in the 5-3-th step, whether the patient has the Parkinson's disease may be diagnosed based on predictive results which occupy the majority, by applying the majority rule to the plurality of predictive results by the plurality of learning models, based on the detected nigrosome-1 region.

As described above, according to the Parkinson's disease diagnosing apparatus and method of the present disclosure, only images including the nigrosome-1 region are classified from the MRI and the nigrosome-1 region is analyzed from the classified image to diagnose the Parkinson's disease.

Further, according to the present disclosure, a visibility of the nigrosome-1 region is improved by applying a susceptibility map weighted imaging protocol and a quantitative susceptibility mapping algorithm and the Parkinson's disease is diagnosed using an image with a visualized substantia nigra structure so that the Parkinson's disease can be more precisely diagnosed using the MRI device commonly supplied and the accuracy of the diagnosis result can be improved.

Further, according to the present disclosure, it is possible to observe only a substantia nigra and a nigrosome-1 region proposed as imaging biomarkers for the Parkinson's disease from an acquired image by additionally performing a pre-processing process, such as angle adjustment, image enlargement, and reslice, on an SMWI image.

Further, according to the present disclosure, it is possible to effectively detect a nigrosome-1 region by detecting a red nucleus and substantia nigra which are more easily detected therearound through machine learning and detecting an image at a moment when both red nucleus and substantia nigra are present and then the red nucleus disappears.

Furthermore, according to the present disclosure, it is possible to make a decision for a final diagnosis as to whether a patient is normal or has a Parkinson's disease according to the majority rule when a plurality of learning models is generated using the same data set and a predictive diagnosis result is derived by applying the plurality of learning models, respectively, and diagnosis results between the plurality of learning models are different.

In addition, a clinical trial for proving drug efficacy is determined by showing a statistical significance indicating whether to achieve a predicted expected effect for clinical trial participants. However, when the Parkinson's disease diagnosing method and apparatus according to the present disclosure is applied, only Parkinson's disease patients exactly targeted by new drugs are included as clinical trial subjects so that the probability of successful clinical trials may be increased as much as possible.

That is, the Parkinson's disease diagnosing method using artificial intelligence according to the present disclosure may be utilized to screen a patient group and a normal group to increase the probability of successful clinical trials.

In the meantime, a technical object to be achieved in the present disclosure is not limited to the aforementioned effects, and other not-mentioned effects will be obviously understood by those skilled in the art from the description below.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Hereinafter, a preferred exemplary embodiment of the present disclosure will be described with reference to the accompanying drawings. The exemplary embodiments which will be described below do not unduly limit the contents of the present disclosure as set forth in the claims and the entire configuration described in the present embodiment cannot be said to be essential as a solution for the present disclosure.

Hereinafter, a Parkinson's disease diagnosing apparatus and method according to a preferred exemplary embodiment of the present invention will be described in detail with reference to the accompanying drawings.

Criterion for Diagnosing Parkinson's Disease by Observing Nigrosome-1 Region in Substantia Nigra First, referring to FIG. 1, a criterion of diagnosing the Parkinson's disease by observing a nigrosome-1 region in a substantia nigra will be described.

Figure 1:
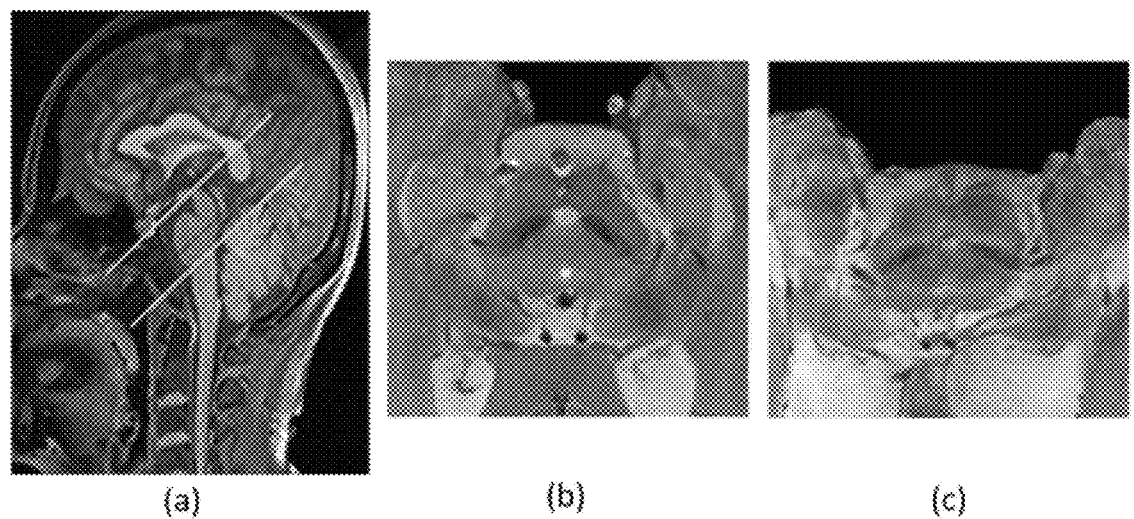
FIG. 1 is a view illustrating an MRI including a substantia nigra and a nigrosome-1 region, with regard to the present disclosure.

FIG. 1 is a view illustrating an MRI including a substantia nigra and a nigrosome-1 region.

FIG. 1A illustrates an imaging slab, FIG. 1B illustrates an image of a substantia nigra and a nigrosome-1 region of normal people, and FIG. 1C illustrates an image of a substantia nigra and a nigrosome-1 region of a Parkinson's disease patient.

The nigrosome-1 region in the substantia nigra of the normal people is illustrated to be black as illustrated in FIG. 1B and the nigrosome-1 region of a patient with the Parkinson's disease is illustrated to be relatively grayish as illustrated in FIG. 1C.

Accordingly, according to the present disclosure, the Parkinson's disease may be diagnosed by observing a shadow of the nigrosome-1 region proposed as imaging biomarkers for the Parkinson's disease in the MRI.

For example, according to the present disclosure, the visibility of the nigrosome-1 region is improved by applying a susceptibility map weighted imaging (hereinafter, abbreviated as "SMWI") protocol and a quantitative susceptibility mapping (hereinafter, abbreviated as "QSM") algorithm therein to analyze whether the nigrosome-1 region is normal to diagnose the Parkinson's disease.

Substantia nigra pars compacta is a midbrain structure including a highly dense population of dopaminergic neurons. These neurons progressively disappear by the idiopathic Parkinson's disease (IPD) to cause disability. This region shows that the iron levels are increased in the IPD patient as compared to a healthy control group.

Recently, as a result of visualizing a small part of the substantia nigra pars compacta known as the nigrosome-1 in a high resolution susceptibility contrast image of a healthy subject, the contrast between the nigrosome-1 and neighboring substantia nigra regions is caused by the difference in iron levels so that the susceptibility difference of two regions is significantly reduced in the IPD patient.

The reduction in the susceptibility difference of two regions as described above has been utilized as imaging biomarkers of the IPD.

Therefore, the nigrosome-1 structure was successfully described in 7T MRI using high resolution (for example, 0.3 mm plane resolution) T2-weighted imaging or susceptibility weighted imaging (SWI).

However, a structure with a significantly reduced contrast is observed from a 3D high resolution T2-weighted imaging due to a limited spatial resolution and signal/contrast to noise ratio (SNR/CNR) in a low magnetic field intensity such as 3T MRI.

This limitation has hindered the reliability and the applicability of the nigrosome-1 imaging in the 3T MRI, despite several successful studies which prove the usefulness of the approach.

Recently, in order to solve the above-described problem, new methods for providing an improved magnetic susceptibility contrast have been proposed.

One of the methods is to couple multi-echo gradient recall echo (hereinafter, referred to as "multi-echo GRE") magnitude images, instead of using a single echo image to improve the SNR, which has a relatively high accuracy in diagnosis of IPD in 3T MRI.

An alternative of the magnitude image may generate artifacts due to blooming of susceptibility weighted imaging (SWI) which uses phase information as a weight mask to increase the susceptibility contrast or the phase imaging.

Another approach related to the susceptibility contrast is a GRE phase (or frequency) image and quantitative susceptibility mapping (QSM) and both are highly susceptible to the susceptibility and have been widely applied in recent years.

Further, a new method which uses a susceptibility weighting mask derived from the QSM for the magnitude image has been proposed.

This approach is similar to the SWI but may solve the blooming artifacts of the SWI and potentially improve the visualization of changes in susceptibility.

The QSM mask weighted imaging has proven to be useful for visualizing the nigrosome-1 structure.

In Non-Patent Document 1, an SMWI technique for neuroimaging is disclosed and in Non-Patent Document 2, an imaging technique of nigrosome-1 in a substantia nigra using multi-echo SMWI in 3T MRI is disclosed. Further, in Non-Patent Document 3, a QSM technique as a means to measure brain iron is disclosed.

Therefore, according to the present invention, the Parkinson's disease is diagnosed based on the change in the nigrosome-1 region due to the Parkinson's disease in accordance with the correlation of a brain iron level and the susceptibility.

Parkinson's Disease Diagnosing Apparatus

Figure 2:
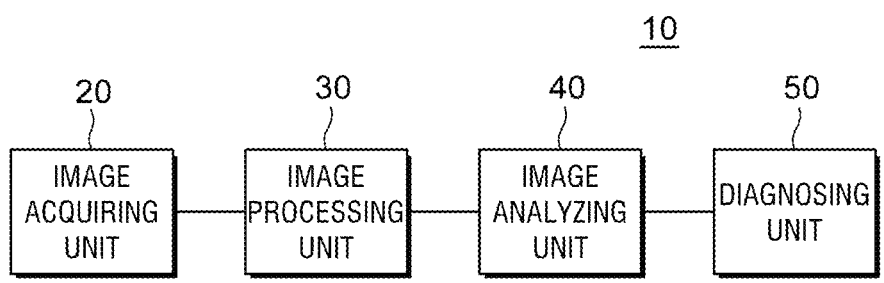
FIG. 2 is a block diagram of a Parkinson's disease diagnosing apparatus according to a preferred exemplary embodiment of the present invention.

FIG. 2 is a block diagram of a Parkinson's disease diagnosing apparatus according to a preferred exemplary embodiment of the present invention.

As illustrated in FIG. 2, a Parkinson's disease diagnosing apparatus 10 according to a preferred exemplary embodiment of the present invention includes an image acquiring unit 20 which acquires multi-echo magnitude and phase images from an MRI obtained by capturing a brain of a patient, an image processing unit 30 which post-processes only a substantia nigra and a nigrosome-1 region proposed as imaging biomarkers of the Parkinson's disease from the acquired image to be observed, an image analyzing unit 40 which analyzes the processed image to classify an image which includes the nigrosome-1 region and detects the nigrosome-1 region from the classified image, and a diagnosing unit 50 which determines whether the nigrosome-1 region is normal in the classified image to diagnose the Parkinson's disease.

Hereinafter, roles and functions of each component will be described in detail with reference to the drawings.

Operation of Image Acquiring Unit and Image Processing Unit

A configuration of an image acquiring unit and an image processing unit will be described in detail with reference to FIG. 3.

Figure 3:
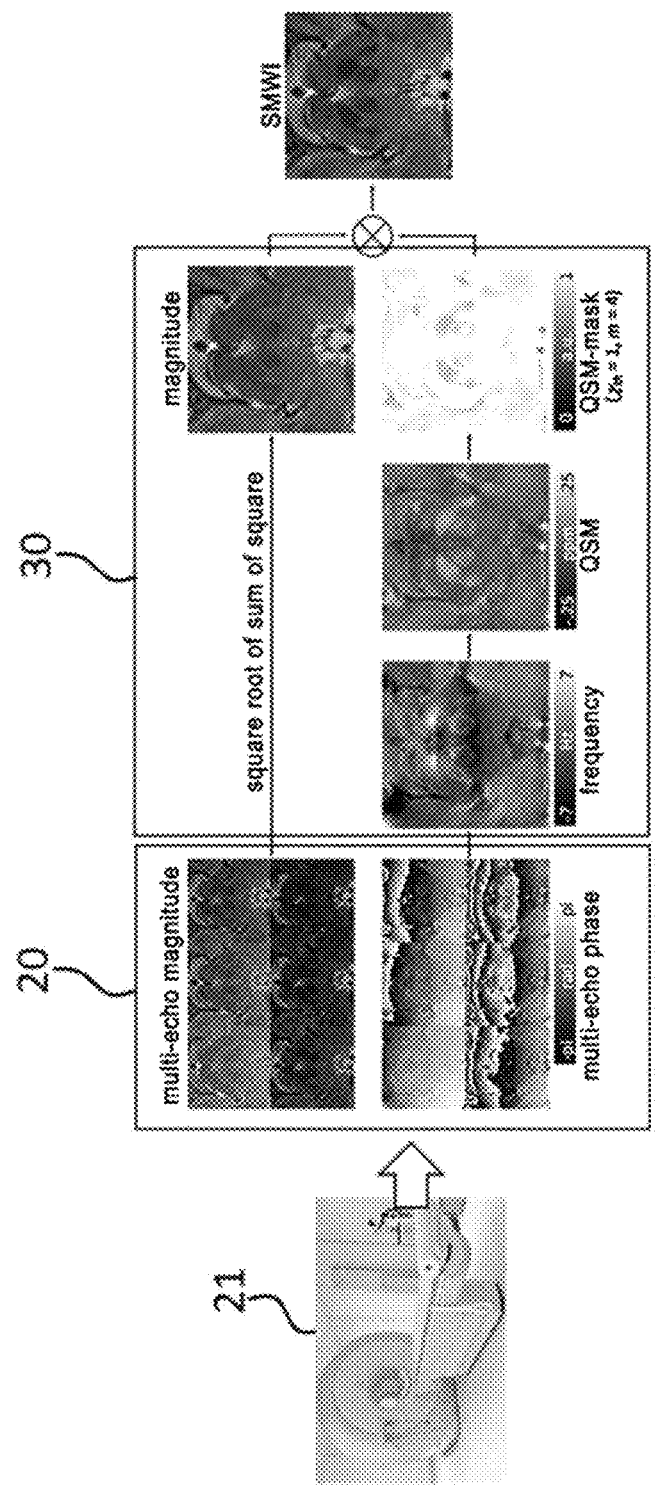
FIG. 3 is a view for explaining operations of an image acquiring unit and an image processing unit according to the present disclosure.

FIG. 3 is a view for explaining operations of an image acquiring unit and an image processing unit. In FIG. 3, a process of generating an SMWI image for the nigrosome-1 structure from a multi-echo composite GRE image is illustrated.

The image acquiring unit 20 is communicatively connected to MRI equipment 21 or a database (not illustrated in the drawing) which stores and controls an MRI captured by the MRI equipment 21, as illustrated in FIG. 3, to acquire an MRI of a patient to diagnose the Parkinson's disease.

The image processing unit 30, as illustrated in FIG. 3, generates an SMWI image from a multi-echo GRE composite image in which a multi-echo magnitude image and a multi-echo phase image are composed, using the QSM algorithm, to visualize the nigrosome-1 structure.

For example, the image processing unit 30 generates a magnitude image which is channel-coupled by a square root of a sum of squares of the multi-channel magnitude images from the multi-channel composite image and the phase image is coupled as a complex average after correcting a global phase offset of individual channels (first step).

The image processing unit 30 combines a single image by a square root of a sum of squares of magnitude images of six echo (second step).

The image processing unit 30 calculates a phase image of different TE using a Laplacian unwrapping algorithm and calculates a frequency w combined in each voxel (third step).

The image processing unit 30 removes a background region from a frequency image using harmonic wave background phase removal using a Laplacian operator method (fourth step).

Here, the QSM may be reconstructed using an improved sparse linear equation and a least-square (iLSQR) method.

For example, in the reconstructed parameter of iLSQR, a tolerance is 0.01, a threshold value $D_{2,\ thres}$ for incomplete k-region mask is 0.1.

Next, the image processing unit 30 further processes a result QSM to generate a QSM mask ($S_{mask}$) for a susceptibility contrast weight (fifth step).

The mask may be generated using Equation 1.

$$S_{mask}(X) = \begin{cases} 0, & X_{th}/X \\ (X_{th} - X)/X_{th} & 0 < X < X_{th} \\ 1, & \text{otherwise} \end{cases}$$ [Equation 1]

Here, X is a quantitative susceptibility value (ppm unit) calculated in the fourth step and $X_{th}$ is a paramagnetic threshold value. The threshold value may be determined using nigrosome-1 imaging data for an optimal CNR later.

Finally, the image processing unit 30 may generate an SMWI image by multiplying a multi-echo composite magnitude image by the QSM mask using the following Equation 2.

$$SMWI = (S_{mask})^m \times mag$$ [Equation 2]

Here, m is the number of multiplications for susceptibility weight and mag is a multi-echo magnitude composite image of the second step.

Further, according to the present disclosure, it is possible to observe only a substantia nigra and a nigrosome-1 region proposed as imaging biomarkers for the Parkinson's disease from an acquired image by additionally performing a pre-process, such as angle adjustment, image enlargement, and reslice, on a generated SMWI image.

Figure 4:
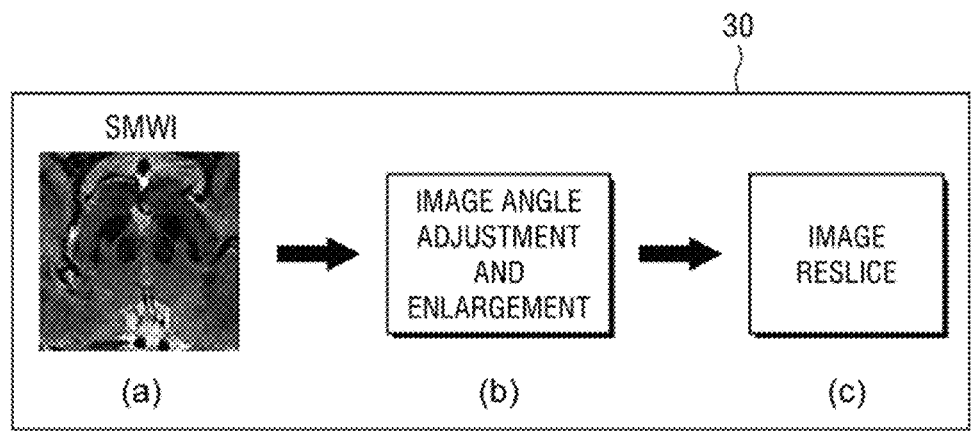
FIG. 4 is a view illustrating an operation of additionally performing a pre-processing process such as angle adjustment, image enlargement, and reslice, on an SMWI image by an image processing unit according to the present disclosure.

FIG. 4 is a view illustrating an operation of additionally performing a pre-processing process, such as an angle adjustment, image enlargement, and reslice, on an SMWI image by an image processing unit according to the present disclosure.

Referring to FIG. 4A, an example of an SMWI image generated by multiplying a multi-echo composite magnitude image by a QSM mask using the above Equation 2 by the image processing unit 30 is illustrated.

Next, as illustrated in FIG. 4B, the image processing unit 30 may perform an angle adjusting operation and an image enlarging operation.

First, the angle adjusting operation of the image processing unit 30 is performed to correct an image misalignment due to a movement of a capturer while capturing images.

Further, the image enlarging operation of the image processing unit 30 is performed to enlarge the nigrosome-1 region.

Specifically, the angle may be adjusted according to the present disclosure such that information on each field value of medical image information (dicom→image orientation patient, image position patient, slice location, and slice thickness) is checked to satisfactorily see the nigrosome-1.

Further, the image enlargement according to the present disclosure may be performed by dividing the entire image into nine equal squares and enlarging a center square area three times horizontally and vertically.

Figure 5:
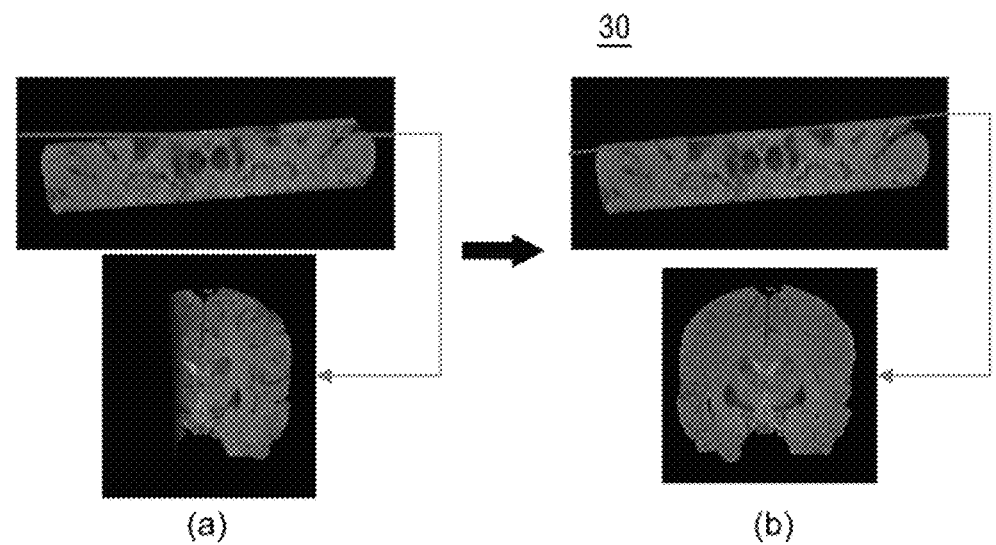
FIG. 5 is a view of an example of a result obtained by adjusting an angle of an SMWI image and enlarging the image by the image processing unit, with regard to FIG. 4.

FIG. 5 is a view of an example of a result obtained by adjusting an angle of an SMWI image and enlarging the image by the image processing unit, with regard to FIG. 4.

Referring to FIG. 5A, an axial image and a red line are represented on a coronal plane and a result obtained by performing the angle adjustment is illustrated in FIG. 5B.

Referring to FIG. 5B, image misalignment due to the movement of the capturer while capturing the images is corrected and an angle is adjusted to satisfactorily see the nigrosome-1, which may be provided by enlarging the nigrosome-1 region by the enlarging operation.

Referring to FIG. 4 again, after performing the angle adjustment and the image enlargement by the image processing unit 30 in FIG. 4B, as illustrated in FIG. 4C, the image processing unit may perform a reslicing process to create more images including the nigrosome-1 region by more finely adjusting a thickness of an MR image.

As described above, the reslicing process is performed to create more images including the nigrosome-1 region by more finely adjusting and applying the thickness of the MR image than the related art.

By means of the reslicing process of the present disclosure, approximately two or three images may be additionally increased so that two or three more images are generated in addition to two or three images which have been generated in the related art. Therefore, approximately two times or more of images including the nigrosome-1 regions may be generated.

Representatively, during the reslicing process according to the present disclosure, a slice thickness of input MR image information is adjusted to be 0.5 or smaller to enlarge an area including the nigrosome-1.

Operation of Image Analyzing Unit

Next, an operation of the image analyzing unit will be described in detail with reference to FIGS. 6 and 7.

Figure 6:
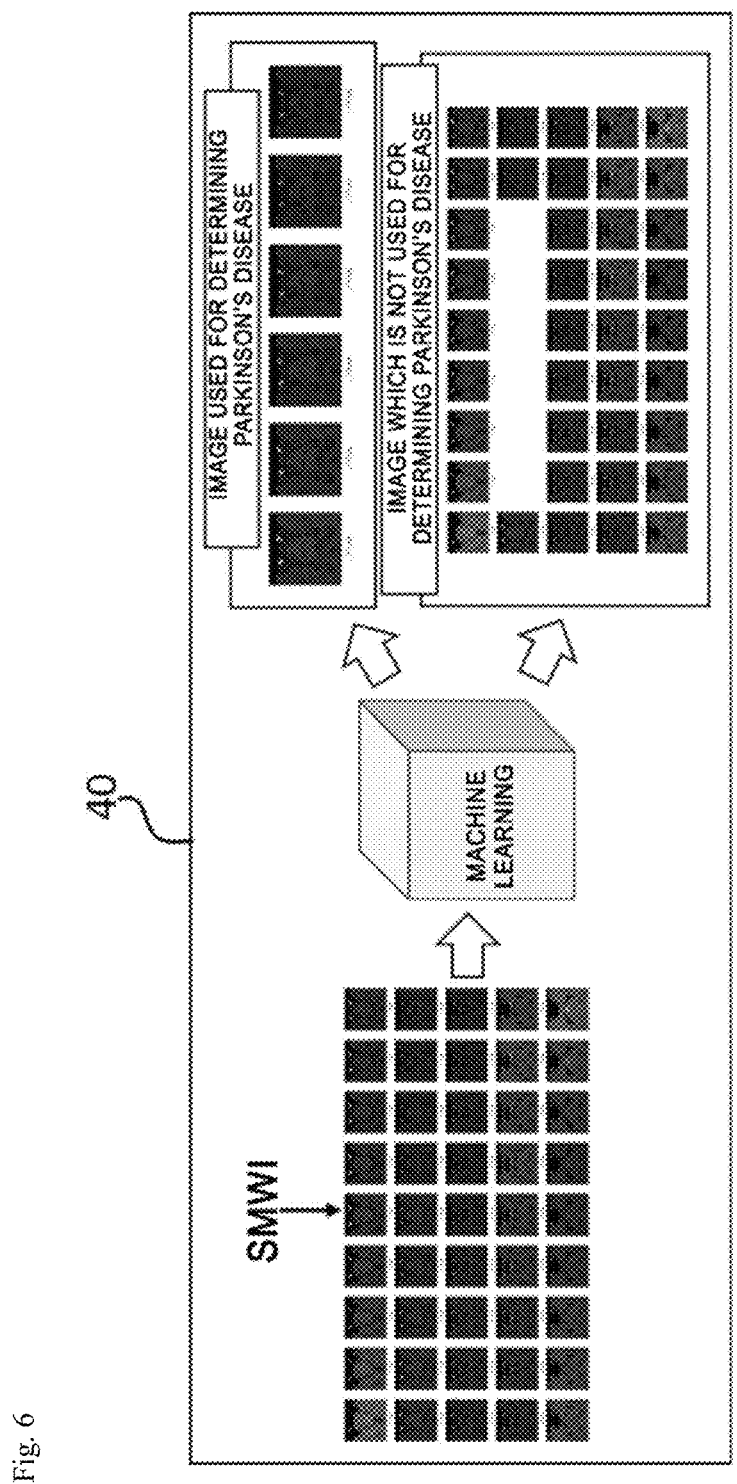
FIGS. 6 and 7 are views for explaining an operation of an image analyzing unit according to the present disclosure.
Figure 7:
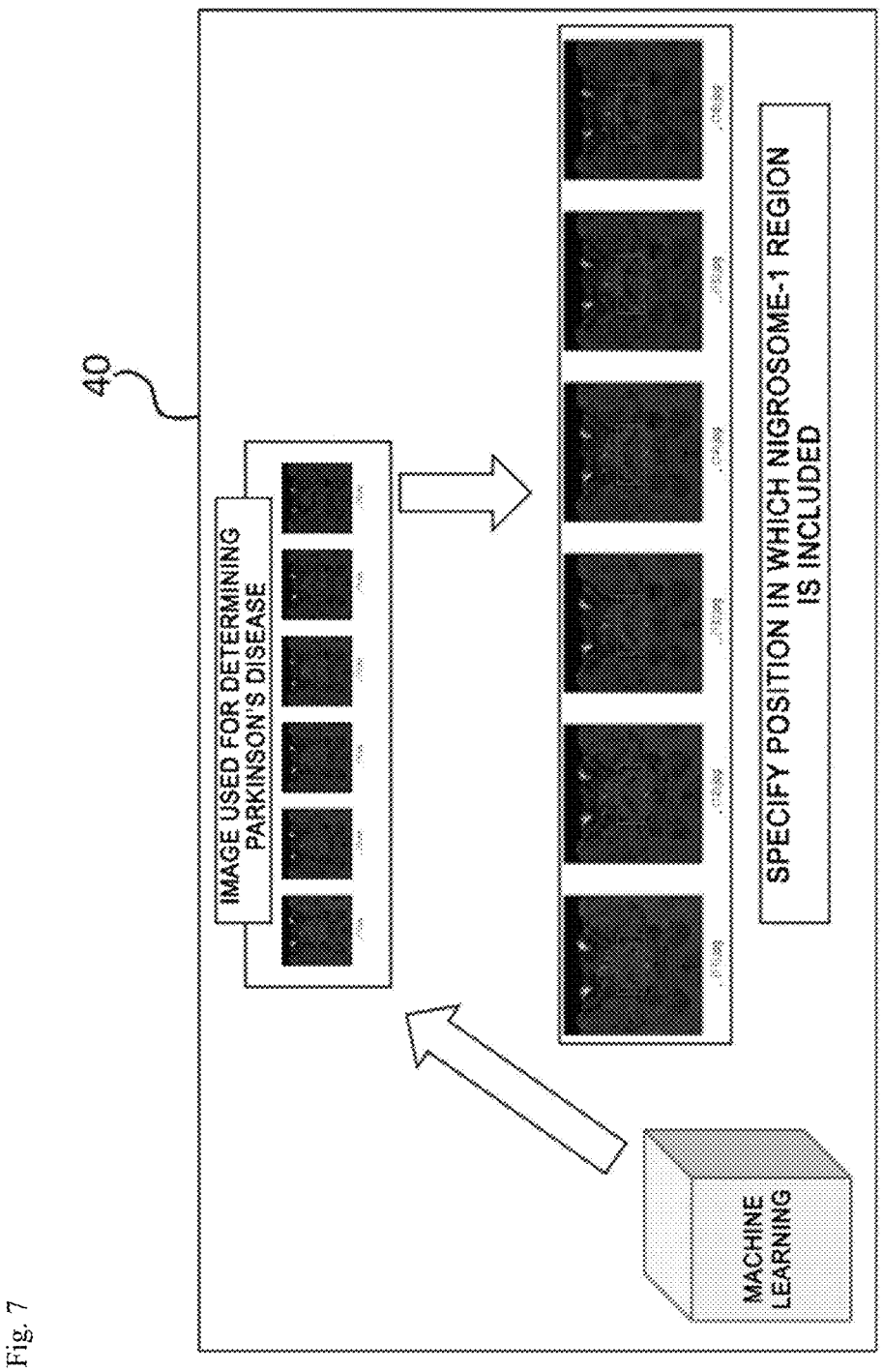

FIGS. 6 and 7 are views for explaining an operation of an image analyzing unit. FIG. 6 illustrates a process of classifying images including a nigrosome-1 region and FIG. 7 illustrates a process of detecting the nigrosome-1 region from the classified images.

As illustrated in FIG. 6, a plurality of SMWI images may be acquired by the post-process of the image processing unit 30.

Generally, the MRI captured for diagnosis of the Parkinson's disease is approximately 40 to 70 sheets for one patient and among them, approximately three to six sheets include the nigrosome-1 region used for diagnosis of the Parkinson's disease.

The image analyzing unit 40 analyzes the image which includes the nigrosome-1 region from the entire MRI through the machine learning to classify an image which includes the nigrosome-1 region and an image which does not include the nigrosome-1 region, as illustrated in FIG. 6.

The image analyzing unit 40 specifies a position where the nigrosome-1 region is included, from each image including the nigrosome-1 region classified by the machine learning and detects the specified nigrosome-1 region, as illustrated in FIG. 7.

For example, the image analyzing unit 40 may classify areas including the nigrosome-1 region using a one-stage detector method, among methods using a deep learning neural network of machine learning.

That is, the image analyzing unit 40 detects a feature map having a feature of a fully convolutional layer from the acquired image using a convolution neural network (hereinafter, abbreviated as "CNN"), configures cross-scale connections by applying a feature pyramid network (hereinafter, abbreviated as "FPN") in the feature map, and optimizes a classification loss, a bounding-box regression loss, and a focal loss to minimize unnecessary classification for a classification result to finally minimize various sizes of images only to images including the nigrosome-1 region.

Figure 8:
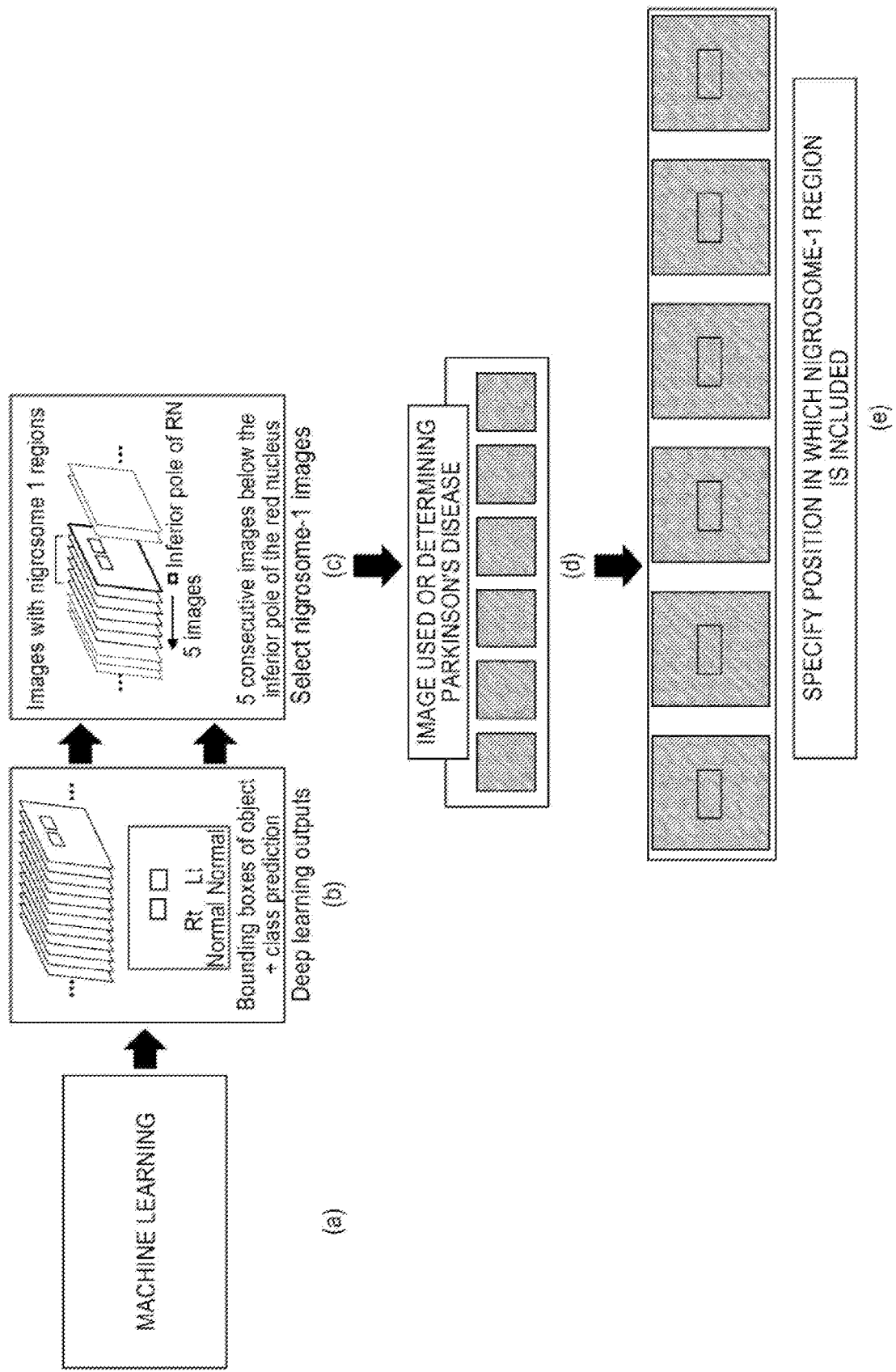
FIG. 8 is a view illustrating a method for more effectively detecting a nigrosome-1 region by an image analyzing unit according to the present disclosure.

FIG. 8 is a view illustrating a method for more effectively detecting a nigrosome-1 region by an image analyzing unit according to the present disclosure;

Referring to FIG. 8, the image analyzing unit 40 according to the present disclosure may effectively detect a nigrosome-1 region by detecting a red nucleus and substantia nigra which are more easily detected therearound through machine learning and detecting an image at a moment when both red nucleus and substantia nigra are present and then the red nucleus disappears.

Referring to FIG. 8A, the image including the nigrosome-1 region is analyzed from the entire MRI through the machine learning to classify an image which includes the nigrosome-1 region and an image which does not include the nigrosome-1 region.

Next, referring to FIG. 8B, in order to specify an area including the nigrosome-1 in an input image, deep learning outputs may be proposed through bounding boxes of objects and class prediction.

According to the present disclosure, in order to detect and analyze positions of the substantia nigra, nigrosome-1, and red nucleus in the input image, a method of generating a feature map which does not lose location information through the CNN neural network and applying the FPN method in the feature map to respond a size change of the object at the time of analysis may be applied.

That is, referring to FIG. 8C, a fact that preprocessed images have a specific position (R0.7 P28.4 F5.2 mm) and a specific angle (C>T39.6>S1.4) may be used based on images associated with the nigrosome-1 regions.

That is, in order to detect a nigrosome-1 region which is necessary to diagnose the Parkinson's disease using a fact that the preprocessed images have a specific position (R0.7 P28.4 F5.2 mm) and a specific angle (C>T39.6>S1.4), red nucleus and substantia nigra which are more easily detected around the nigrosome-1 may be detected first through the machine learning.

Specifically, referring to FIG. 8C, images are sequentially checked in an inferior direction and an image at the moment when both the red nucleus and substantia nigra are present and then the red nucleus disappears may be detected.

Thereafter, on the premise that the nigrosome-1 region is present in about 2 to 3 mm of slices from the detected image, a number of 2 to 3 mm thick images including the nigrosome-1 region may be detected from the entire MR images (for example, 5 to 6 sheets).

At least one image is selected from 2 to 3 mm thick images including the nigrosome-1 region and referring to FIGS. 8D and 8E, a location where a nigrosome-1 region is present is specified from each classified image including the nigrosome-1 region and the specified nigrosome-1 region may be detected.

Operation of Diagnosing Unit

Next, referring to FIGS. 9 and 10, an operation of the diagnosing unit 50 according to the present disclosure will be described.

Figure 9:
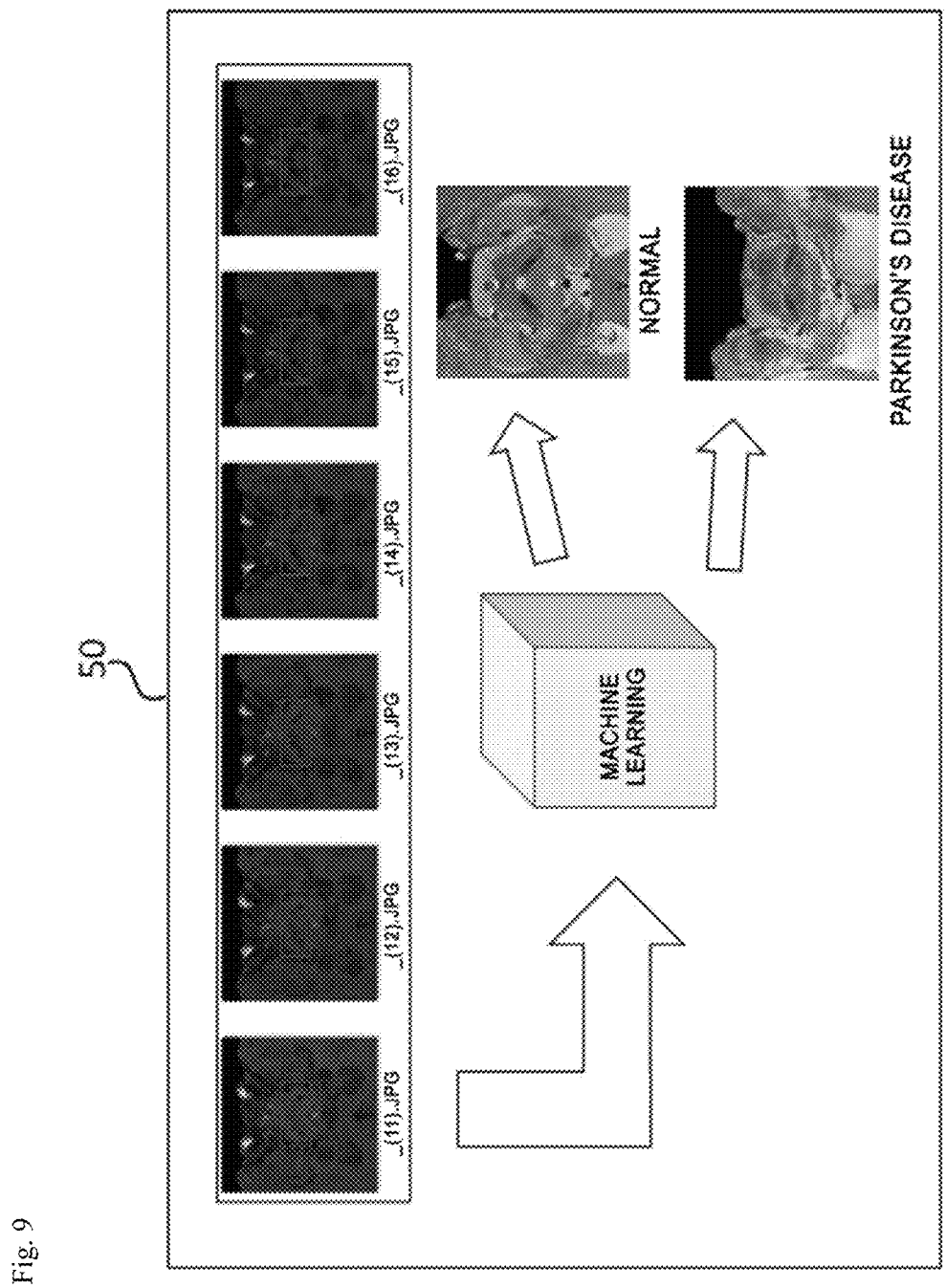
FIG. 9 is a view illustrating an operation of a diagnosing unit according to the present disclosure.
Figure 10:
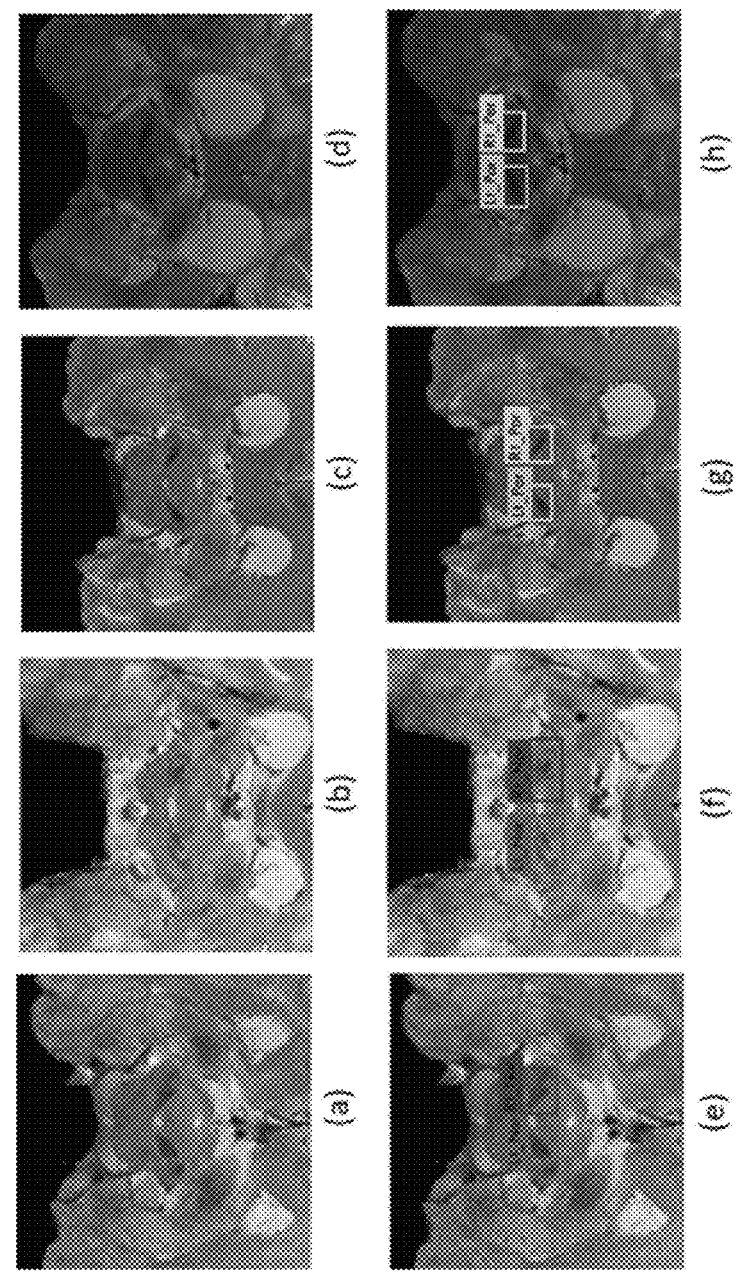
FIG. 10 is a view illustrating a state in which a diagnosis result is applied to an input image, with regard to the present disclosure.

FIG. 9 is a view for explaining an operation of a diagnosing unit and FIG. 10 is a view illustrating a state in which a diagnosis result is applied to an input image.

As illustrated in FIG. 9, the diagnosing unit 50 may analyze whether the nigrosome-1 region detected by the image analyzing unit 40 is normal through the machine learning to diagnose the Parkinson's disease.

For example, a diagnosis result may be applied as illustrated in FIGS. 10E to 10H in accordance with a result of diagnosing whether it is a Parkinson's disease from the input image of FIGS. 10A to 10D.

In the meantime, according to the present disclosure, in order to improve a diagnostic performance, a method of making a decision by combining a plurality of prediction results by the diagnosing unit 50 may be applied.

Figure 11:
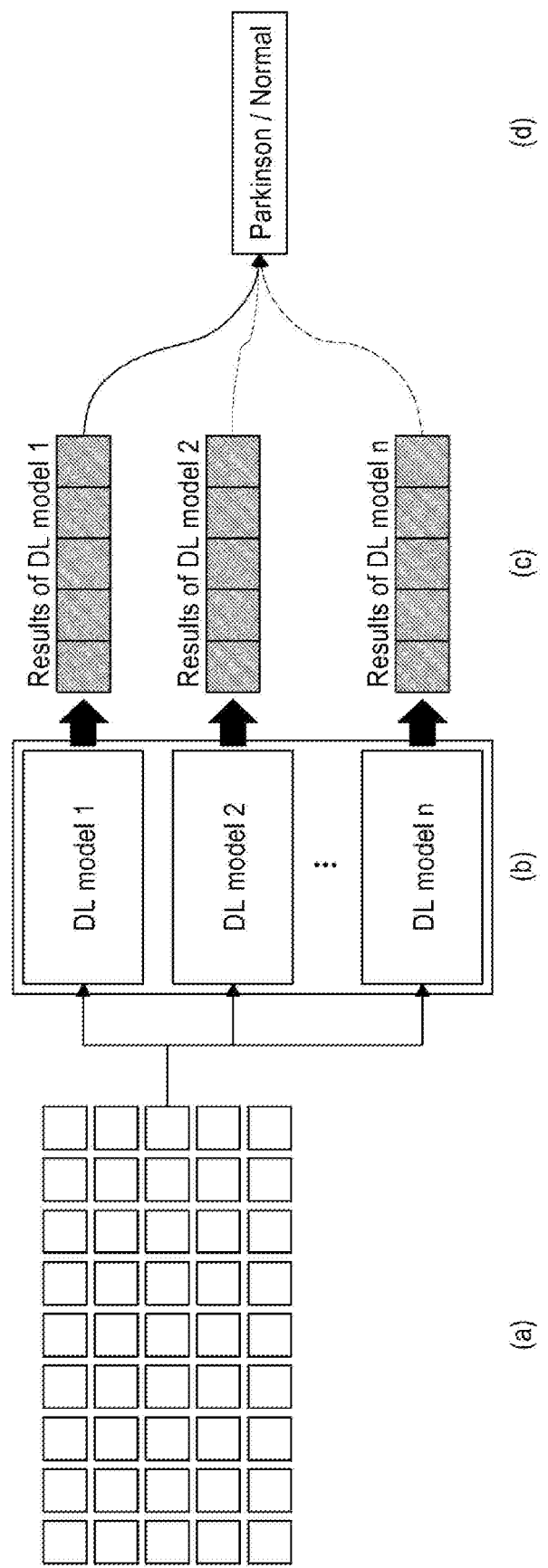
FIG. 11 is a view illustrating a method for improving a diagnostic performance by combining a plurality of prediction results by a diagnosing unit according to the present disclosure.

FIG. 11 is a view illustrating a method for improving a diagnostic performance by combining a plurality of prediction results by a diagnosing unit according to the present disclosure.

Referring to FIG. 11, as illustrated in FIG. 11B, a plurality of learning models may be generated based on the same data set SET illustrated in FIG. 11A.

Further, as illustrated in FIG. 11C, predictive diagnosis results when the plurality of learning models is applied are derived and referring to FIG. 11D, when the diagnosis results of the plurality of learning models are different from each other, a final diagnosis as to whether it is normal or Parkinson's disease may be made according to the majority rule.

Therefore, when the diagnosis results between the models are different, the final diagnosis is decided according to the majority rule so that predictive results of the plurality of deep learning models are combined to finally diagnose whether the subject is normal or a patient. Therefore, the diagnostic performance may be improved.

Parkinson's Disease Diagnosing Method

Next, a Parkinson's disease diagnosing method according to a preferred exemplary embodiment of the present invention will be described in detail with reference to FIG. 12.

Figure 12:
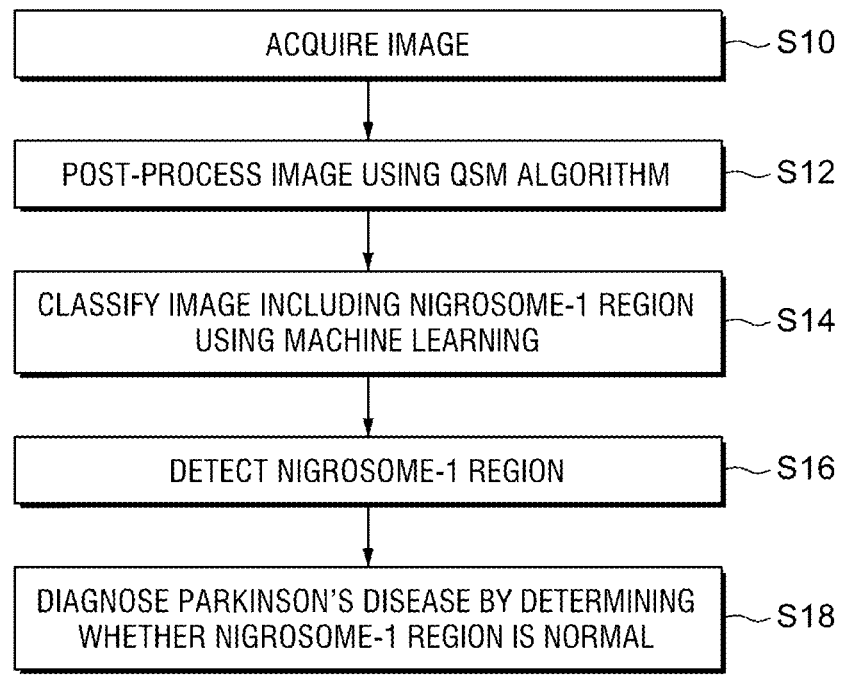
FIG. 12 is a flowchart for explaining a Parkinson's disease diagnosing method according to a preferred exemplary embodiment of the present disclosure step by step.

FIG. 12 is a flowchart for explaining a Parkinson's disease diagnosing method according to a preferred exemplary embodiment of the present invention step by step.

In step S10 of FIG. 12, the image acquiring unit 20 acquires a plurality of MRIs of a patient to diagnose the Parkinson's disease through the communication with the MRI equipment 21 or the database.

Here, the image acquiring unit 20 may acquire a multi-echo GRE composite image in which a multi-echo magnitude image and a multi-echo phase image are composed, from 3T MRI.

In step S12, the image processing unit 30 generates an SMWI image by post-processing a multi-echo GRE composite image in which a multi-echo magnitude image and a multi-echo phase image are composed, using the QSM algorithm, to visualize the nigrosome-1 structure.

In step S14, the image analyzing unit 40 analyzes the image including the nigrosome-1 region from the entire MRI through the machine learning to classify an image which includes the nigrosome-1 region and an image which does not include the nigrosome-1 region.

The image analyzing unit 40 specifies a position where the nigrosome-1 region is included, from each image which includes the nigrosome-1 region classified by the machine learning and detects the specified nigrosome-1 region (S16).

Finally, the diagnosing unit 50 determines whether the nigrosome-1 region detected from each image classified as an image which includes the nigrosome-1 region in the image analyzing unit 40 is normal to diagnose the Parkinson's disease (S18).

Hereinafter, specific processes of steps S12, S14, S16, and S18 will be described in detail with reference to the drawings.

Process (S12) of Generating SMWI Image by Post-Processing

Figure 13:
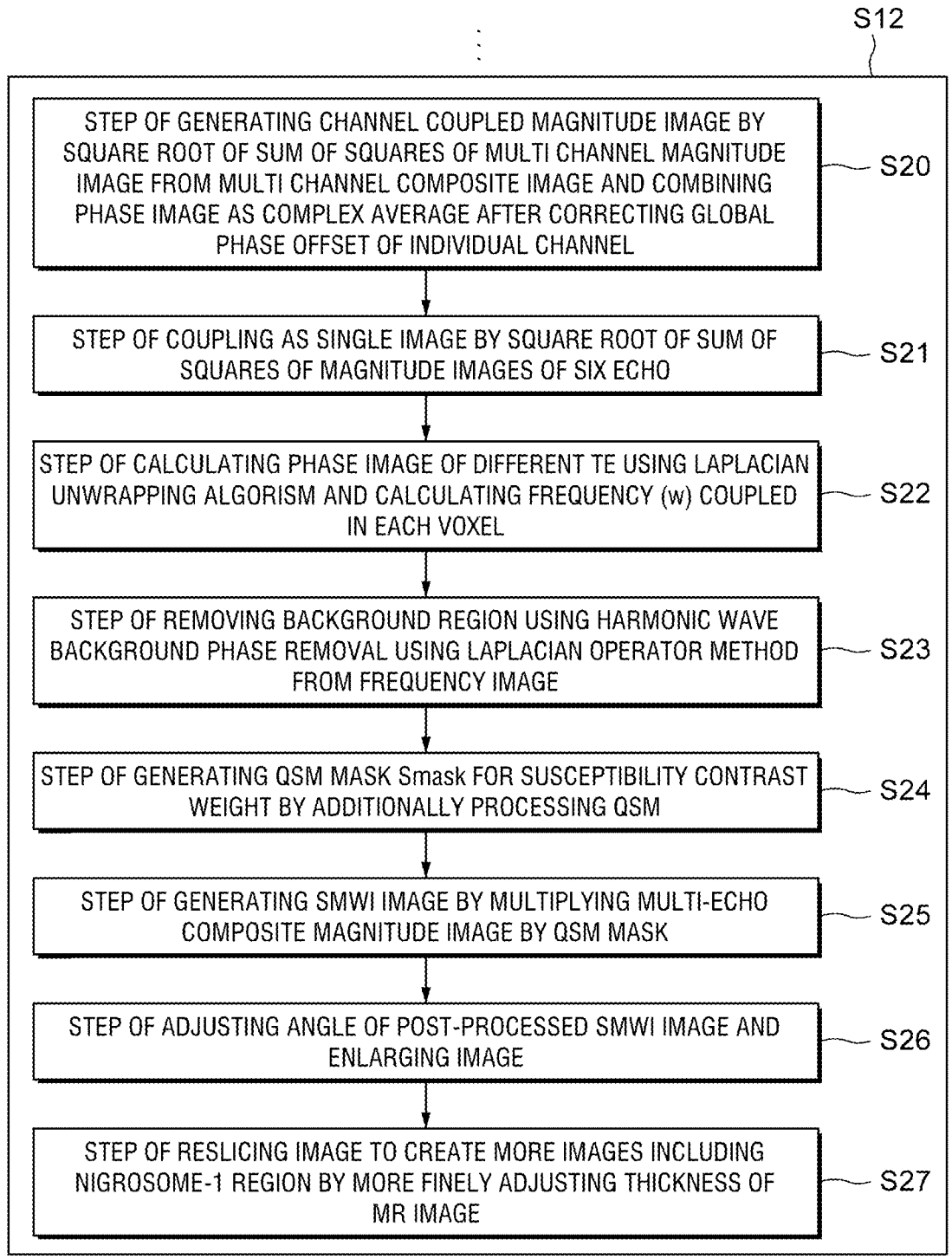
FIG. 13 is a flowchart for explaining a post-processing process to observe a substantia nigra and a nigrosome-1 region proposed as imaging biomarkers of a Parkinson's disease from an image acquired according to a preferred exemplary embodiment of the present disclosure.

FIG. 13 is a flowchart for explaining a post-processing process to observe a substantia nigra and a nigrosome-1 region proposed as imaging biomarkers of a Parkinson's disease from an image acquired according to a preferred exemplary embodiment of the present disclosure.

Referring to FIG. 13, specific steps of S12 process in which the above-described image processing unit 30 generates an SMWI image by post-processing a multi-echo GRE composite image in which a multi-echo magnitude image and a multi-echo phase image are composed, using the QSM algorithm, to visualize the nigrosome-1 structure are illustrated.

First, a step S20 of generating a channel-coupled magnitude image by a square root of a sum of squares of the multi-channel magnitude image from the multi-channel composite image and coupling the phase image as a complex average after correcting a global phase offset of individual channels is performed.

Next, a step S21 of coupling as a single image by a square root of a sum of squares of magnitude images of six echo is performed.

After the step S21, a step S22 of calculating a phase image of different TE using a Laplacian unwrapping algorithm and calculating a frequency w combined in each voxel is performed.

Further, a step S23 of removing a background region from the frequency image using a harmonic wave background phase removal using a Laplacian operator method is performed.

Next, a step S24 of generating a QSM mask Smask for susceptibility contrast weight by additionally processing the QSM and then a step S25 of generating the SMWI image by multiplying the multi-echo composite magnitude image by the QSM mask are performed.

Further, after performing a step S26 of adjusting an image angle and enlarging the image on the post-processed SMWI image, a step S27 of reslicing images to make more images including the nigrosome-1 region by more finely adjusting the thickness of the MR image is performed. Therefore, a process of post-processing the substantia nigra and nigrosome-1 region which are proposed as imaging biomarkers of the Parkinson's disease to be observed from the acquired image is performed.

Process of Classifying Image Including Nigrosome-1 Region and Image which does not Include Nigrosome-1 Region (S14) and Detecting Specified Nigrosome-1 Region (S16)

Figure 14:
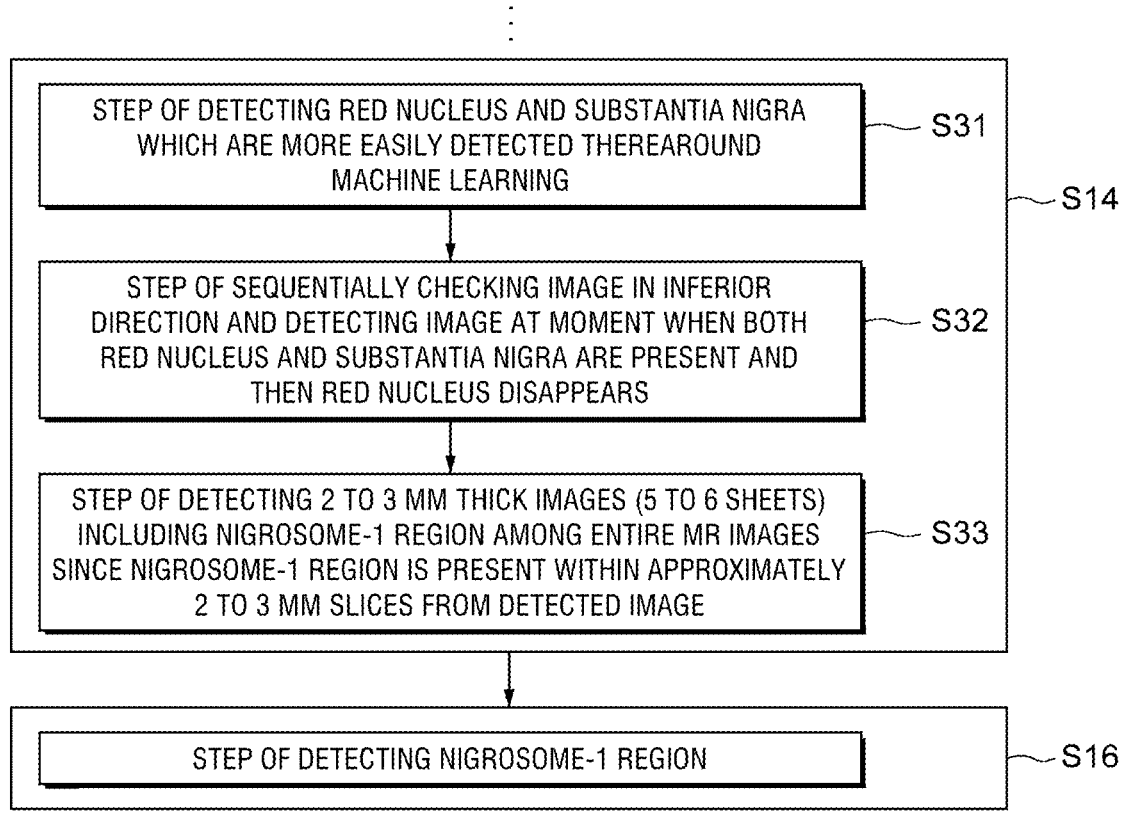
FIG. 14 is a flowchart for explaining a method of classifying an image including a nigrosome-1 region by analyzing an image processed according to a preferred exemplary embodiment of the present disclosure and detecting the nigrosome-1 region from the classified image.

FIG. 14 is a flowchart for explaining a method of classifying an image including a nigrosome-1 region by analyzing an image processed according to a preferred exemplary embodiment of the present disclosure and detecting the nigrosome-1 region from the classified image.

Referring to FIG. 14, a process of classifying images including the nigrosome-1 region and images which do not include the nigrosome-1 region (S14) and a process of detecting a specified nigrosome-1 region (S16) are specifically illustrated.

First, a step S31 of detecting red nucleus and substantia nigra which are more easily detected therearound is performed through the machine learning.

Next, a step S32 of sequentially checking images in the inferior direction and detecting an image at a moment when both red nucleus and substantia nigra are present and then the red nucleus disappears is performed.

Since the nigrosome-1 region is present within approximately 2 to 3 mm slice from the detected image, a step S33 of detecting 2 to 3 mm thick images (5 to 6 sheets) including the nigrosome-1 region from the entire MR image is performed.

After the step S33, a step S16 of detecting the nigrosome-1 region by at least one of images derived by the step S33 is performed.

Figure 15:
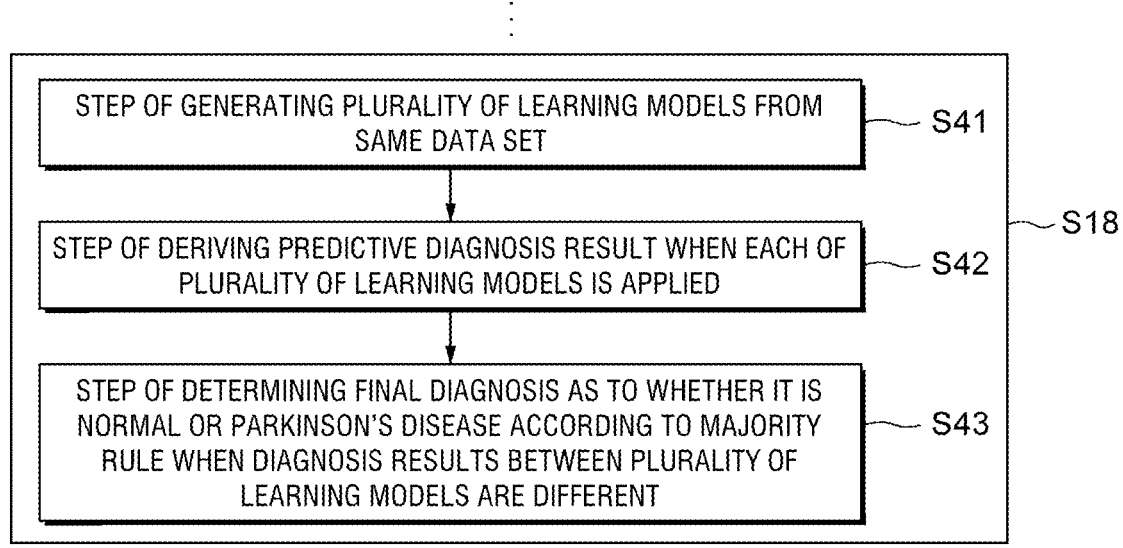
FIG. 15 is a flowchart for explaining a process of determining whether the nigrosome-1 region is normal in the classified image to diagnose the Parkinson's disease.

Process (S18) of Diagnosing Whether it is Parkinson's Disease by Determining Whether Detected Nigrosome-1 Region is Normal FIG. 15 is a flowchart for explaining a process of determining whether the nigrosome-1 region is normal in the classified image to diagnose the Parkinson's disease.

Referring to FIG. 15, a step S41 of generating a plurality of learning models with the same data set SET is performed first and a predictive diagnosis result when the plurality of learning models is applied, respectively, is derived (S42).

In this case, the diagnosis results between the plurality of learning models may be different from each other so that in the present disclosure, a final diagnosis as to whether a patient is normal or has a Parkinson's disease is decided according to majority rule (S43).

Therefore, when the diagnosis results between the models are different, the final diagnosis is decided according to the majority rule so that predictive results of the plurality of deep learning models are combined to finally diagnose whether the subject is normal or a patient. Therefore, the diagnostic performance may be improved.

Method of Increasing Probability of Successful Clinical Trial by Utilizing Parkinson's Disease Diagnosing Method Using Artificial Intelligence to Screen Patient Group and Normal Group The Parkinson's disease diagnosing method and apparatus according to the present disclosure are utilized to screen the patient group and the normal group to increase a probability of successful clinical trials.

That is, the present disclosure may provide a device, a system, and a method of utilizing the Parkinson's disease diagnosing method using artificial intelligence to screen a patient group and a normal group to increase the probability of successful clinical trials.

A result of clinical trials for demonstration of drug efficacy is determined by showing a statistical significance indicating whether to achieve a predicted expected effect for clinical trial participants. However, when the Parkinson's disease diagnosing method and apparatus according to the present disclosure are applied, only Parkinson's disease patients exactly targeted by new drugs are included as clinical trial subjects so that the probability of successful clinical trials may be increased as much as possible.

First, problems of existing new drug clinical trials will be described in advance.

A result of clinical trials for demonstration of drug efficacy is determined by showing a statistical significance indicating whether to achieve a predicted expected effect for clinical trial participants.

In the case of the Parkinson's disease, it is inevitable to rely on UPDRS evaluation, neurological examination, and Hoehn & Yarr stage evaluation (0 to 5 stages) to measure whether symptoms are improved by the drug efficacy. However, these methods are based on questionnaire and have problems in that the scale of data is not detailed.

Therefore, in order to prove the statistical significance, a numerical value of an evaluation scale needs to be statistically significantly increased before and after medication or as compared to a placebo group. The higher the predicted increase value, the smaller the number of target subjects and the higher the probability of achieving statistical significance.

In this case, if the predicted increase value is small, the number of target subjects increases as well, and the difficulty of statistical proof is increased.

As a result, it is very difficult to increase one step of evaluation scale of the Parkinson's disease, so that there is a problem in that a possibility of passing the clinical trial is very low.

In the present disclosure, in order to solve the above-described problem, only Parkinson's disease patients exactly targeted by the new drug are included as subjects of the clinical trials to increase a probability of successful clinical trials as much as possible.

One of important failure factors in a new drug development process for central nervous system drugs is the difficulty of screening the correct subjects and selecting a drug response group.

Since a response rate to the placebo for the central nervous system drugs is particularly high, an important strategy of increasing the success rate is to reduce the heterogeneity of the subject group and set a biomarker capable of predicting a drug reactivity.

Further, since it takes a long time to confirm the Parkinson's disease (approximately three months), a screening test is difficult so that there is a problem in that it is very difficult to include only the Parkinson's disease patients targeted by new drugs as subjects of clinical trials.

Therefore, the Parkinson's disease diagnosing method using artificial intelligence proposed by the present disclosure may be utilized to screen a patient group and a normal group to increase the probability of successful clinical trials.

Figure 16:
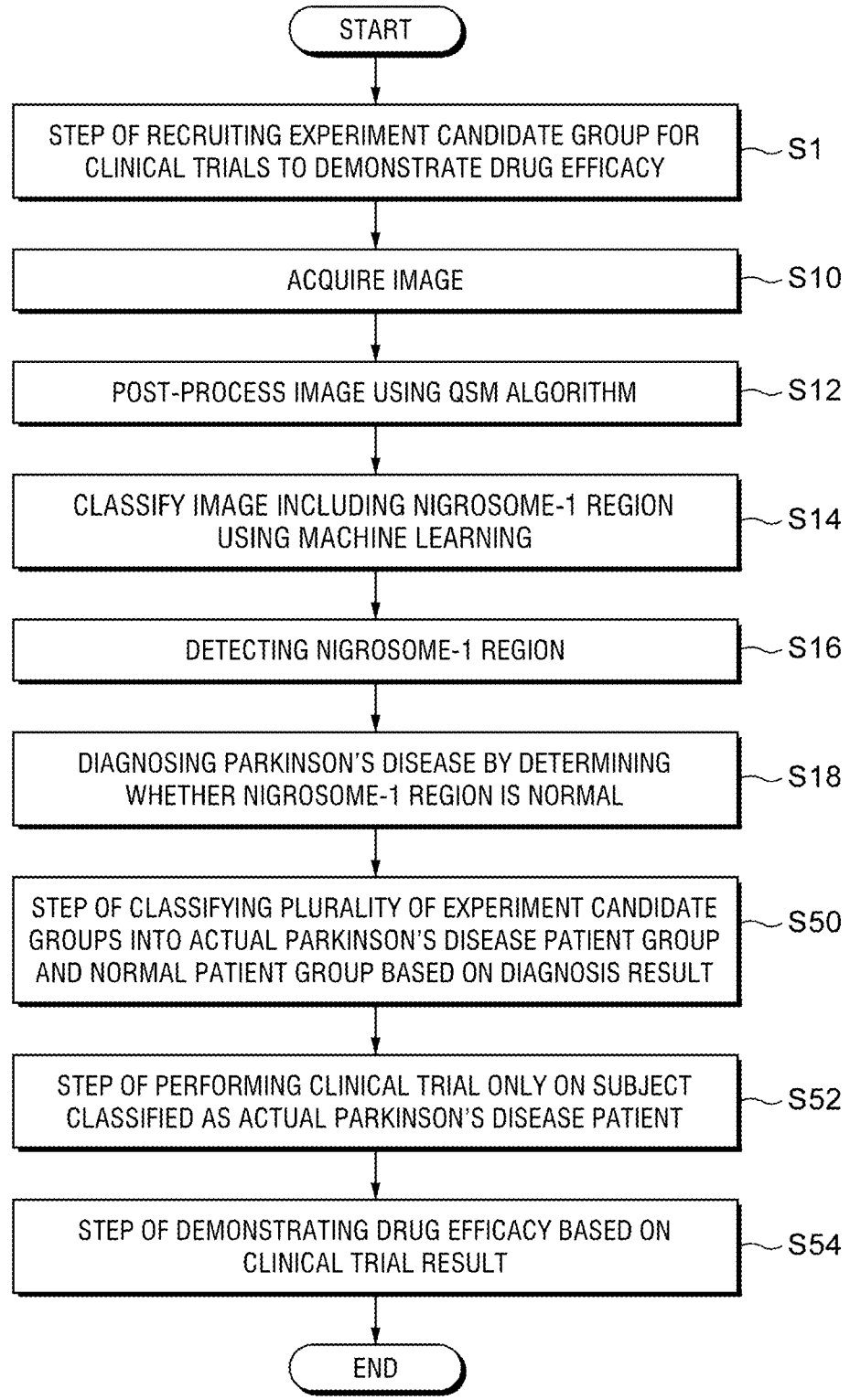
FIG. 16 is a view for explaining a method of increasing a probability of successful clinical trials by utilizing a Parkinson's disease diagnosing method using artificial intelligence to screen a patient group and a normal group.

FIG. 16 is a view for explaining a method of increasing a probability of successful clinical trials by utilizing a Parkinson's disease diagnosing method using artificial intelligence to screen a patient group and a normal group.

Referring to FIG. 16, first, a step S1 of recruiting an experiment candidate group for a clinical trial to demonstrate a drug efficacy is performed.

Next, a step S10 of acquiring images from a plurality of experiment candidate groups, a step S12 of post-processing an image by applying a QSM algorithm to each image, a step S14 of classifying images including a nigrosome-1 region using machine learning, a step S16 of detecting the nigrosome-1 region, and a step S18 of diagnosing whether a Parkinson's disease is present based on whether the nigrosome-1 region is normal are performed.

The steps S10 to S18 have been described above with reference to FIGS. 12 to 15 so that for simplicity of the specification, a redundant description will be omitted.

Next, when a diagnosis result is derived through the step S18, a step S50 of classifying the plurality of experimental candidate groups into an actual Parkinson's disease patient group and a normal patient group based on the diagnosis result may be performed.

In this case, a step S52 of performing a clinical trial and a step S54 of demonstrating a drug efficacy based on a clinical trial result are performed only on the subject classified as the actual Parkinson's disease patient group. Therefore, only the Parkinson's disease patients exactly targeted by the new drug are included as clinical trial subjects so that the probability of successful clinical trial may be increased.

As a result, the Parkinson's disease diagnosing method using artificial intelligence according to the present disclosure may be utilized to screen a patient group and a normal group to increase the probability of successful clinical trials.

The above-described steps S1 to S54 may be independently performed by the Parkinson's disease diagnosing apparatus 10 or may be applied by providing a separate server (not illustrated) or a separate central control device (not illustrated) to perform the entire operations together with the Parkinson's disease diagnosing apparatus 10.

According to the Parkinson's disease diagnosing apparatus and method of the present invention, only images including the nigrosome-1 region are classified from the MRI and the nigrosome-1 region is analyzed from the classified image to diagnose the Parkinson's disease.

Further, according to the present invention, a visibility of the nigrosome-1 region is improved by applying a susceptibility map weighted imaging protocol and a quantitative susceptibility mapping algorithm and the Parkinson's disease is diagnosed using an image with a visualized substantia nigra structure so that the Parkinson's disease may be more precisely diagnosed using the MRI equipment commonly supplied and the accuracy of the diagnosis result may be improved.

Further, according to the present disclosure, it is possible to observe only a substantia nigra and a nigrosome-1 region proposed as imaging biomarkers for the Parkinson's disease from an acquired image by additionally performing a pre-processing process, such as angle adjustment, image enlargement, and reslice, on an SMWI image.

Further, according to the present disclosure, it is possible to effectively detect a nigrosome-1 region by detecting a red nucleus and a substantia nigra which are more easily detected therearound through machine learning and detecting an image at a moment when both red nucleus and substantia nigra are present and then the red nucleus disappears.

Furthermore, according to the present disclosure, it is possible to make a decision for a final diagnosis as to whether a patient is normal or has a Parkinson's disease according to the majority rule when a plurality of learning models is generated using the same data set SET and a predictive diagnosis result is derived by applying the plurality of learning models and diagnosis results between the plurality of learning models are different.

In addition, a result of clinical trials for demonstration of drug efficacy is determined by showing a statistical significance indicating whether to achieve a predicted expected effect for clinical trial participants. However, when the Parkinson's disease diagnosing method and apparatus according to the present disclosure are applied, only Parkinson's disease patients exactly targeted by new drugs are included as clinical trial subjects so that the probability of successful clinical trials may be increased as much as possible.

That is, the Parkinson's disease diagnosing method using artificial intelligence according to the present disclosure may be utilized to screen a patient group and a normal group to increase the probability of successful clinical trials.

A technical object to be achieved in the present disclosure is not limited to the aforementioned effects, and other not-mentioned effects will be obviously understood by those skilled in the art from the description below.

The above-described exemplary embodiments of the present invention may be implemented through various methods. For example, the exemplary embodiments of the present disclosure may be implemented by a hardware, a firm ware, a software, or a combination thereof.

When the exemplary embodiment is implemented by the hardware, the method according to the exemplary embodiment of the present disclosure may be implemented by one or more of application specific integrated circuits (ASICs), digital signal processors (DSPs), digital signal processing devices (DSPDs), programmable logic devices (PLDs), field programmable gate arrays (FPGAs), a processor, a controller, a microcontroller, or a microprocessor.

When the exemplary embodiment is implemented by the firmware or the software, the method according to the exemplary embodiment of the present disclosure may be implemented by a module, a procedure, or a function which performs a function or operations described above. The software code is stored in the memory unit to be driven by the processor. The memory unit is located inside or outside the processor and exchanges data with the processor, by various known units.

As described above, the detailed description of the preferred exemplary embodiments of the disclosed present invention is provided such that those skilled in the art implement and carry out the present invention. While the invention has been described with reference to the preferred exemplary embodiments, it will be understood by those skilled in the art that various changes and modifications of the present invention may be made without departing from the spirit and scope of the invention. For example, those skilled in the art may use configurations disclosed in the above-described exemplary embodiments by combining them with each other. Therefore, the present invention is not intended to be limited to the above-described exemplary embodiments but to assign the widest scope consistent with disclosed principles and novel features.

The present invention may be implemented in another specific form within the scope without departing from the spirit and essential feature of the present invention. Therefore, the detailed description should not restrictively be analyzed in all aspects and should be exemplarily considered. The scope of the present invention should be determined by rational interpretation of the appended claims and all changes are included in the scope of the present invention within the equivalent scope of the present invention. The present invention is not intended to be limited to the above-described exemplary embodiments but to assign the widest scope consistent with disclosed principles and novel features. Further, claims having no clear quoting relation in the claims are combined to configure the embodiment or may be included as new claims by correction after application.

What is claimed is:

1. An apparatus for detecting Parkinson's disease, the apparatus comprising:
   a memory comprising one or more instructions; and
   a processor configured to execute the one or more instruction to:
   acquire a plurality of first images by scanning a brain of a patient using magnetic resonance imaging, the plurality of first images being multi-echo magnitude and phase images;
   post-process the acquired plurality of first images by:
   generating a plurality of susceptibility map weighted imaging images by applying a quantitative suscep-tibility map mask to the plurality of first images based on a quantitative susceptibility mapping algorithm; and
   performing one or more of angle adjustment, image enlargement, or reslice, on the plurality of generated susceptibility map weighted imaging images;
   analyze the plurality of post-processed first images to obtain a plurality of second images that are classified as including the nigrosome-1 region and detect the nigrosome-1 region of the plurality of second images, the plurality of second images being classified by detecting a red nucleus and a substantia nigra present in the plurality of post-processed first images through machine learning and sequentially analyzing the plurality of post-processed first images to identify at which image the detected red nucleus disappears; and
   determine, whether the detected nigrosome-1 region in the plurality of second images is normal.

2. The apparatus for detecting Parkinson's disease according to claim 1, wherein:
   the angle adjustment is an operation of correcting a misalignment of the plurality of generated susceptibility map weighted imaging images caused by movement of the patient,
   the image enlargement is an operation of enlarging to a nigrosome-1 region in the plurality of generated susceptibility map weighted imaging images, and
   the reslice is an operation of obtaining additional susceptibility map weighted imaging images of the nigrosome-1 region by generating images having a smaller slice thickness that an slice thickness of the plurality of generated susceptibility map weighted imaging images.

3. The apparatus for detecting Parkinson's disease according to claim 1, wherein the plurality of second images are classified by also identifying at which image the detected red nucleus appears when sequentially analyzing the plurality of post-processed first images.

4. The apparatus for detecting Parkinson's disease according to claim 1, wherein the processor is further configured to classify the plurality of second images using a one-stage detector method among methods using a deep learning neural network of machine learning.

5. The apparatus for detecting Parkinson's disease according to claim 4, wherein the processor is further configured to detect a feature map having a feature of a fully convolutional layer by applying a convolutional neural network (CNN) to the plurality of post-processed first images, derive cross-scale connections by applying a feature pyramid network (FPN) to the feature map, and adjust a classification loss, a bounding-box regression loss, and a focal loss for a classification result based on the cross-scale connections to classify the plurality of second images.

6. The apparatus for detecting Parkinson's disease according to claim 1, wherein the processor is further configured to generate a plurality of learning models to determine whether an input image indicates Parkinson's disease, based on a same data set, derive a plurality of predictive results by the plurality of learning models, based on the detected nigrosome-1 region, and determine whether the patient has the Parkinson's disease based on the plurality of predictive results.

7. The apparatus for detecting Parkinson's disease according to claim 6, wherein the processor is further configured to determine whether the patient has the Parkinson's disease based on predictive results, among the plurality of predictive results, which occupy a majority, by applying a majority rule to the plurality of predictive results derived by the plurality of learning models, based on the detected nigrosome-1 region.

8. An method of providing information for detecting Parkinson's disease, the method comprising:
- a first step of acquiring a plurality of first images by scanning a brain of a patient using magnetic resonance imaging, the plurality of first images being multi-echo magnitude and phase images;
- a second step of generating a plurality of post-processed first images the by:
  - generating a plurality of susceptibility map weighted imaging images by applying a quantitative susceptibility map mask to the plurality of first images based on a quantitative susceptibility mapping algorithm; and
  - performing one or more operation of angle adjustment, image enlargement, and reslice, on the generated susceptibility map weighted imaging image;
- a third step of analyzing the plurality of post-processed first images to obtain a plurality of second images that are classified as including the nigrosome-1 region, the nigrosome-1 region of the plurality of second images being classified by detecting a red nucleus and a substantia nigra present in the plurality of post-processed first images by machine learning and sequentially analyzing the plurality of post-processed first images to identify at which image the detected red nucleus disappears;
- a fourth step of detecting the nigrosome-1 region of the classified second image; and
- a fifth step of providing information on the detected nigrosome-1 region to that indicates whether the patient has Parkinson's disease.

9. The method according to claim 8, wherein:
the angle adjustment is an operation of correcting a misalignment of the plurality of generated susceptibility map weighted imaging images caused by movement of the patient,
the image enlargement is an operation of enlarging the nigrosome-1 region in the plurality of generated susceptibility map weighted imaging images, and
the reslice is an operation of obtaining additional susceptibility map weighted imaging images of the nigrosome-1 region by generating images having a smaller slice thickness that an slice thickness of the plurality of generated susceptibility map weighted imaging images.

10. The method according to claim 8, wherein the plurality of second images are classified by also identifying at which image the detected red nucleus appears when sequentially analyzing the plurality of post-processed first images.

11. The method according to claim 8, wherein in the third step, the second image including the nigrosome-1 region is classified using a one-stage detector method among methods using a deep learning neural network of machine learning.

12. The method according to claim 11, wherein the third step comprises:
- a 3-1-th step of detecting a feature map having a feature of a fully convolutional layer by applying a convolutional neural network (CNN) to the plurality of post-processed first images;
- a 3-2-th step of deriving cross-scale connections by applying a feature pyramid network (FPN) to the feature map; and
- a 3-3-th step of adjusting a classification loss, a bounding-box regression loss, and a focal loss for a classification result based on the cross-scale connections to classify the plurality second images.

* * * * *